US012575838B2

(12) United States Patent
Von Zeppelin et al.

(10) Patent No.: US 12,575,838 B2
(45) Date of Patent: Mar. 17, 2026

(54) PERFORATOR

(71) Applicant: ADEOR MEDICAL AG, Valley (DE)

(72) Inventors: Fabio Von Zeppelin, Valley (DE);
Johann Fersterer, Valley (DE)

(73) Assignee: ADEOR MEDICAL AG, Valley (DE)

( * ) Notice: Subject to any disclaimer, the term of this patent is extended or adjusted under 35 U.S.C. 154(b) by 214 days.

(21) Appl. No.: 18/253,678

(22) PCT Filed: Nov. 19, 2021

(86) PCT No.: PCT/EP2021/082346
§ 371 (c)(1),
(2) Date: May 19, 2023

(87) PCT Pub. No.: WO2022/106643
PCT Pub. Date: May 27, 2022

(65) Prior Publication Data
US 2024/0000464 A1 Jan. 4, 2024

(30) Foreign Application Priority Data
Nov. 20, 2020 (GB) ..................................... 2018314

(51) Int. Cl.
A61B 17/16 (2006.01)

(52) U.S. Cl.
CPC ................................ A61B 17/1695 (2013.01)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1633; A61B 17/1635; A61B 17/1637; A61B 17/1655; A61B 17/1657; A61B 17/1662; A61B 17/1695; B23B 51/04; B23B 51/0411; B23B 51/0413; B23B 51/0417; B23B 51/0426; B23B 51/044; B23B 51/0461; B23B 51/0466; B23B 51/0467
See application file for complete search history.

(56) References Cited

U.S. PATENT DOCUMENTS

| | | | | |
|---|---|---|---|---|
| 1,859,547 A | * | 5/1932 | Young | B23B 51/044 408/137 |
| 4,456,010 A | * | 6/1984 | Reimels | B23B 51/10 408/139 |

(Continued)

FOREIGN PATENT DOCUMENTS

| | | | | |
|---|---|---|---|---|
| CN | 204890099 U | | 12/2015 | |
| CN | 111134767 A | * | 5/2020 | A61B 17/147 |

(Continued)

*Primary Examiner* — Eric S Gibson
(74) *Attorney, Agent, or Firm* — Dinsmore & Shohl LLP

(57) ABSTRACT

A perforator for cutting a hole in bone tissue is provided. The perforator comprises an anchor, a hole cutter configured to rotate around the anchor, and conversion means for converting rotational motion of the hole cutter around the anchor into linear motion of the hole cutter towards the material to be cut. The invention is usable to cut holes in a wide variety of materials, in particular for a perforator for cutting a hole in a skull of a human or animal. A kit of parts and a method of cutting a hole are also provided.

16 Claims, 12 Drawing Sheets

(56)     References Cited

U.S. PATENT DOCUMENTS

| | | | | | |
|---|---|---|---|---|---|
| 4,830,001 | A * | 5/1989 | Walus | ............... | B29C 66/53241 |
| | | | | | 408/139 |
| 5,876,405 | A * | 3/1999 | Del Rio | ............. | A61B 17/1695 |
| | | | | | 606/80 |
| 5,993,453 | A * | 11/1999 | Bullara | .................. | A61B 17/16 |
| | | | | | 606/86 R |
| 8,328,477 | B2 * | 12/2012 | Allen | ................. | B23B 51/0473 |
| | | | | | 408/233 |
| 8,371,777 | B2 * | 2/2013 | Allen | ................. | B23B 51/0426 |
| | | | | | 408/233 |
| 9,339,874 | B2 * | 5/2016 | Allen | .................... | B27G 15/00 |
| 9,919,364 | B2 * | 3/2018 | Allen | ................. | B23B 51/0426 |
| 10,618,119 | B2 * | 4/2020 | Allen | ................. | B23B 51/0426 |
| 2009/0087273 | A1 * | 4/2009 | Allen | ................. | B23B 51/0473 |
| | | | | | 408/208 |
| 2010/0322733 | A1 * | 12/2010 | Allen | ................. | B23B 51/0473 |
| | | | | | 408/231 |
| 2011/0177472 | A1 * | 7/2011 | Lee | ................... | A61B 17/1695 |
| | | | | | 433/114 |
| 2011/0223558 | A1 * | 9/2011 | Anitua Aldecoa | ... | A61C 8/0089 |
| | | | | | 433/167 |
| 2013/0136553 | A1 * | 5/2013 | Allen | ..................... | B27G 15/00 |
| | | | | | 408/226 |
| 2016/0256938 | A1 * | 9/2016 | Allen | ................. | B23B 51/0426 |
| 2018/0311749 | A1 * | 11/2018 | Allen | ................. | B23B 51/0473 |
| 2024/0000464 | A1 * | 1/2024 | Von Zeppelin | .... | A61B 17/1617 |

FOREIGN PATENT DOCUMENTS

| | | | | | |
|---|---|---|---|---|---|
| CN | 111184552 | A | | 5/2020 | |
| CN | 113974762 | A * | | 1/2022 | |
| CN | 118557251 | A * | | 8/2024 | |
| DE | 102022128754 | A1 * | 5/2024 | ............... | B22F 1/17 |
| EP | 2138255 | A2 * | 12/2009 | ......... | A61B 17/1637 |
| EP | 3501708 | A1 * | 6/2019 | ......... | B23B 51/0461 |
| EP | 3804638 | A2 | 4/2021 | | |
| EP | 4360785 | A1 * | 5/2024 | ............... | B22F 1/17 |
| EP | 3727729 | B1 * | 7/2024 | ......... | B23B 51/0461 |
| GB | 2181076 | A * | 4/1987 | ......... | A61B 17/1695 |
| GB | 2597512 | A * | 2/2022 | ......... | A61B 17/1695 |
| GB | 2601302 | A * | 6/2022 | ......... | A61B 17/1617 |
| WO | WO-9913782 | A1 * | 3/1999 | ......... | A61B 17/1695 |
| WO | WO-2007049012 | A1 * | 5/2007 | ......... | B23B 51/0426 |
| WO | WO-2010013900 | A2 * | 2/2010 | ......... | A61B 17/1688 |
| WO | 2015150844 | A1 | 10/2015 | | |
| WO | WO-2016059608 | A1 * | 4/2016 | ......... | A61B 17/1633 |
| WO | WO-2019120886 | A1 * | 6/2019 | ......... | B23B 51/0461 |
| WO | WO-2019121139 | A1 * | 6/2019 | ......... | B23B 51/0461 |
| WO | WO-2022106643 | A1 * | 5/2022 | ......... | A61B 17/1617 |

* cited by examiner 406                                                    206

A

402

404

400

700

700

800

1000

1004

1002

202     204

1000

1003

1005

204

202

1006

PERFORATOR

CROSS-REFERENCE TO RELATED APPLICATIONS

This application is the U.S. National Stage of PCT/EP2021/082346 filed on Nov. 19, 2021, which claims priority to United Kingdom Patent Application 2018314.1 filed on Nov. 20, 2020, the entire content of both are incorporated herein by reference in their entirety.

FIELD OF THE INVENTION

The present invention relates to a perforator for cutting a hole in bone tissue. In a particularly preferred embodiment the invention relates to a perforator for cutting a hole in a skull of a human or animal.

BACKGROUND OF THE INVENTION

In order to carry out surgical operations inside the cranial cavity, it is necessary to first obtain access to the cranial cavity by drilling one or more holes through the bone of the skull (the cranium). The process of drilling a hole through the skull is called trepanation. Trepanation is a difficult and delicate procedure, as sufficient force must be applied to the drill head for it to advance through the hard layers of bone tissue, but the drill head must be halted immediately after perforation of the skull in order to avoid the drill head damaging the dura mater or soft tissue inside the cranium.

Prior art perforators have typically been similar to conventional drills, in that a forward force or pressure must be applied to the drill to drive the drill head through the skull. A major risk with such prior art designs is that when the cranium is perforated, the forward force or pressure on the drill head can drive the drill head inwards through the newly created hole and into the cranium, potentially causing potential damage to the dura mater.

Attempts to reduce this risk of damage to the dura mater have focused on stopping rotation of the drill head as soon as the cranium is perforated, so that the rotating cutting or drill head does not tear or otherwise damage the dura mater. In order to provide a perforator in which the rotation of the drill head stops as soon as the cranium has been perforated, cranial perforators are provided in the prior art in which the drill head is not permanently coupled to a drive shaft of an electric drill.

Well-known examples of prior art designs are disclosed in U.S. Pat. No. 4,456,010 and International Patent Application No. WO 2015/150844. The drill of U.S. Pat. No. 4,456,010 comprises an inner drill head, an outer drill head arranged coaxially around the inner drill head, and a drive shaft, all rotatable about the same axis of rotation. The inner drill head is biased away from the drive shaft with a spring, so that when there is no pressure applied to the tip of the inner drill head, the drill head and the shaft are disconnected, and neither of the inner or outer drill heads rotates even when the drive shaft is rotating. Connection of the inner drill head to the drive shaft is controlled using a slot-and-pin type clutch that comprises a slot in the distal end of the drive shaft, and a corresponding pin in the proximal end of the drill head. The clutch-pin also extends into a triangular slot in the wall of the outer drill head.

As the inner drill head of U.S. Pat. No. 4,456,010 is pressed against bone in use, a force is applied which moves the inner drill head against the biasing spring until the clutch-pin in the inner drill head engages with the slot in the rotating drive shaft. In this position, the clutch-pin also extends into a triangular slot in the wall of the outer drill head and engages with the apex of the triangular slot, so that rotational force is transmitted from the drive shaft via the inner drill head to the outer drill head, and both drill heads rotate together. As long as sufficient force is applied to the tip of the inner drill head to overcome the biasing force of the spring such that the clutch-pin remains engaged with the slot, the rotating drive shaft of the electric drill transmits rotational force to the inner and outer drill heads so that both drill heads rotate and the perforator drills through the bone. As soon as the inner drill head perforates the inner surface of the cranium, however, force is no longer applied to the drill head by the bone, so the biasing spring urges the inner drill head forward and forces the clutch-pin out of the slot in the drive shaft. Both the inner and outer drill heads should then cease to rotate immediately, to prevent damage to the dura mater.

As sufficient force is applied to the tip of the inner drill head to overcome the biasing force of the spring for the perforator to drill bone, for the clutch to disengage, the skull must be perforated. Even when the release mechanism in the perforator separates immediately, which cannot always be guaranteed due to the high contact pressure and sliding friction between the slot and the pin, the inner drill head penetrates the skull as it is urged forward by the spring once the skull is perforated.

As the prior art perforator cuts the skull, the drill heads are configured to shred or grate the bone being cut. After the cranial cavity has been accessed, the hole in the skull must then be filled with an artificial substance to seal the skull to protect a patient's brain from damage.

The prior art design of WO 2015/150844 replaces the slot-and-pin clutch of U.S. Pat. No. 4,456,010 with two square-sided first connecting profiles on the proximal end of the drill head, and two square-sided second connecting profiles on the distal end of the drive shaft. Nevertheless, this prior art design also requires sufficient force to be applied to the tip of the inner drill head to overcome the biasing force of the spring.

The penetration depth of prior art perforators is up to 5 mm, most commonly 3 or 4 mm. This penetration depth, and failure of the release mechanism to separate immediate, causes dura or brain injuries in about 1% of trepanations. Additionally, prior art perforators are highly complex, and to secure safe cooperation of the various components, high process reliability is required, which increases costs.

Similar risks of damage to underlying material are present in a variety of technical fields other than surgical operations. For example, when cutting holes in walls made of plaster, plasterboard, wood or similar materials, there is a significant risk of damage to electrical cables and pipes that are positioned behind the wall material being cut. Prior art tools such as hole cutter drill bits are designed to be mounted to an electrical drill in order to cut wide holes through material such as plasterboard, but as these tools require the user to apply forward pressure to the drill, it is easy to inadvertently damage utilities positioned on the far side of the plasterboard sheet.

The inventors have appreciated the need for an apparatus for cutting a hole, such as a perforator, in which there is a reduced risk of damage to anything underlying the material to be cut by the apparatus, or in which the risk is eliminated completely. The inventors have further appreciated the need for a less complex apparatus for cutting holes. The inventors have further appreciated the need for an apparatus which facilitates sealing of a hole after it has been cut.

SUMMARY OF THE INVENTION

The invention provides a perforator for cutting a hole, a kit of parts for cutting a hole, and a method of cutting a hole, as defined herein, to which reference should now be made. Preferred or advantageous features of the invention are described herein.

The invention may provide an apparatus for cutting a hole. The apparatus may comprise an anchor configured to be secured to a material to be cut, and a hole cutter configured to rotate around the anchor and cut the material. The apparatus may further comprise conversion means for converting rotational motion of the hole cutter around the anchor into linear motion of the hole cutter towards the material, wherein the hole cutter is configured to engage the anchor via the conversion means. The apparatus may advantageously be usable to cut holes in a wide variety of materials, but in a particularly preferred embodiment the invention relates to a perforator for cutting a hole in bone tissue, for example in the a skull of a human or animal.

In a first aspect, the invention provides a perforator for cutting a hole in bone tissue. The perforator comprises an anchor configured to be secured to a material to be cut, and a hole cutter configured to rotate around the anchor and cut the material. The perforator further comprises conversion means for converting rotational motion of the hole cutter around the anchor into linear motion of the hole cutter towards the material, wherein the hole cutter is configured to engage the anchor via the conversion means.

The material to be cut is preferably bone tissue.

The perforator comprises an anchor configured to be secured to bone tissue to be cut or perforated, and a hole cutter configured to rotate around the anchor and cut the bone tissue. The perforator further comprises conversion means for converting rotational motion of the hole cutter around the anchor into linear motion of the hole cutter towards the bone tissue, wherein the hole cutter is configured to engage the anchor via the conversion means.

The anchor preferably comprises a distal end configured to be secured to bone tissue to be cut or perforated. The conversion means is preferably configured to convert rotational motion of the hole cutter around the anchor into linear motion of the hole cutter towards the distal end of the anchor.

The term "rotational" refers herein to rotation around a longitudinal axis of the anchor and/or the hole cutter.

The perforator is suitable for cutting holes in bone tissue, and may additionally be suitable for cutting holes in a variety of materials to be cut. Preferably the material to be cut may be a rigid or semi-rigid material, so that the anchor can be secured to the material and, upon rotation of the hole cutter around the anchor, the material may produce a counterforce/traction on the anchor to allow the conversion means to convert rotation of the hole cutter around the anchor into linear motion of the hole cutter towards, into, and eventually through the material.

In the following, the perforator of the present invention may alternatively be referred to as an apparatus.

In contrast to the prior art perforators, the apparatus of the present invention may be used without a separate electric drill. The apparatus of the present invention may be a standalone apparatus for cutting a hole, which may be manually operated. As such, the problems in relation to clutches of prior art perforators, which connect a perforator with the drive shaft of an electric drill, are avoided, and complexity is significantly reduced.

As the perforator for cutting a hole is secured directly to the material to be cut via the anchor, and the conversion means converts rotational motion of the hole cutter into linear motion towards the material, once the anchor has been secured to the material to be cut, the user is not required to exert any force in the direction of the material to be cut for the hole cutter to cut the material. In other words, the user does not have to push the hole cutter towards the material to be cut. Rather, the user need only apply rotational force to the hole cutter, and the conversion means converts this rotational motion to drive the hole cutter into and through the material as it rotates.

In contrast, for prior art perforators, a force must be exerted on the tip of the inner drill head so as to overcome the biasing force of the spring, requiring the user to exert a force in the direction of the material to be cut. This means that in the prior art perforators the user must press the drill head towards the cranium at all times during drilling, which increases the risk of accidentally pushing the drill through the newly cut hole when the cranium is finally perforated.

As the perforator of the present invention does not require the user to exert a force towards the material in order to cut the hole, this advantageously eliminates any risk of the user exerting excessive force towards the skull during cutting. Such excessive force may result in a bone flap being cut breaking off prematurely or the perforator penetrating the skull too deeply.

The conversion means is configured to convert rotational motion of the hole cutter around the anchor into linear motion of the hole cutter towards the material to be cut. This preferably occurs only upon there being a sufficient counterforce (or traction), away from the material, acting on the anchor. This counterforce is only present while the disc of material being cut is still sufficiently connected to the rest of the material, as once the disc of material is fully separated from the rest of the material, the material can no longer exert a counterforce on the anchor.

Advantageously, this means that unlike the cutting heads of the perforators of the prior art, any linear motion of the hole cutter towards the material to be cut is arrested as soon as a material being cut, or bone flap, is separated from the rest of the material (or bone). In this way, as soon as the apparatus has successfully drilled a hole, i.e. a piece of the material to be cut has been successfully (mostly or completely) separated from the rest of the material, the linear motion of the hole cutter is halted, and any rotation motion occurs in a plane of the material to be cut. That is, even if a user continues to rotate the hole cutter, there will be no further linear motion of the hole cutter through the material. Any further rotation of the hole cutter will simply rotate the anchor and the disc of cut material within the hole. This means that there is no need for the hole cutter to completely penetrate the material to be cut, e.g. for the perforator to penetrate into the skull. As such, there is no danger of any cutting edge of the hole cutter damaging anything underlying the material to be cut, e.g. the dura mater.

The linear motion of the hole cutter towards the material may be arrested before the piece of material being cut has been separated completely from the rest of the material, as the counterforce/traction acting on the anchor may fall significantly when the piece of material has been mostly separated from the rest of the material. As such, a thin remnant (a layer of material) may remain within the hole. Alternatively, the counterforce/traction may be sufficient and the hole cutter configured such that the material to be cut is penetrated completely.

As the perforator of the present invention reduces, or eliminates, any risk of the perforator penetrating the material to be cut, the apparatus may advantageously be used for robotically-assisted cutting of a hole. For example, a robotic manipulator may be used to secure the anchor to the material to be cut and/or to rotate the hole cutter around the anchor to cut the material and/or to remove the apparatus from the material. The configuration of the apparatus may allow for robotically-assisted operation techniques to be employed.

Preferably, the hole cutter comprises at least one cutting edge at a radius r from a central axis A of the anchor, so that conversion of rotational motion of the hole cutter around the anchor urges the hole cutter towards the material and causes the hole cutter to cut a hole with a diameter d=2r.

The apparatus is preferably configured to cut a hole by cutting around the perimeter of a disc of the material to be cut. The anchor is fixed to the centre of the disc of material being cut, and the disc cut from the material has a diameter of d=2r, in order to create a hole of the same size in the material being cut. As the hole cutter rotates around the anchor, and is urged through the material as it cuts, the hole cutter cuts around a perimeter of a disc of material being separated from the rest of the material. When the cutter has cut through the material to be cut, the anchor remains attached to the disc of material which can then be removed to leave a hole.

The diameter d may vary widely depending on the material that the apparatus is intended to cut.

In preferred embodiments of the invention, diameter d is less than 70 mm, more preferably less than 60 mm, yet more preferably less than 30 mm.

Particularly preferably, diameter d is less than 14 mm, or less than 12 mm, for example between about 4 mm and about 14 mm. More preferably, diameter d is between about 5 mm and about 12 mm. Yet more preferably, diameter d is about 6 mm or 8 mm or 11 mm.

Advantageously, a hole having a specific, selectable diameter may be drilled. This may be particularly advantageous for perforators. A hole of a diameter required for a specific operative procedure may be selected and a corresponding hole cutter used. A diameter d of 11 mm may be particularly suitable for a perforator.

The conversion means and anchor may be compatible with hole cutters having a range of diameters. As such, a single anchor may be configured to be selectively used with different hole cutters configured to cut holes of differing diameter.

The at least one cutting edge of the hole cutter may be off-set axially so as to provide cavities for chippings of the material. This allows for chippings of the material being cut to be transported away from the hole being cut.

The clearance angle of the at least one cutting edge may be between about 5 degrees and 35 degrees, preferably between about 10 degrees and about 25 degrees, and more preferably between about 15 degrees and about 20 degrees.

The at least one cutting edge may have a width of between about 0.5 mm and about 1.5 mm, preferably between about 0.8 mm and about 1.3 mm, and more preferably between about 1.0 mm and about 1.2 mm.

The conversion means may alternatively be termed a conversion mechanism, a motion-conversion mechanism or a rotation-conversion mechanism.

The conversion means is preferably configured to progressively urge the hole cutter into the material to be cut as the hole cutter rotates around the anchor. The rotational motion of the hole cutter cuts the material, and the conversion means progressively drives the rotating hole cutter further through the thickness of the material to be cut. The conversion means is therefore configured to convert rotational motion of the hole cutter around the anchor into both linear motion of the hole cutter towards the material in addition to the continued rotational motion of the hole cutter around the anchor.

Preferably, the conversion means comprises a first portion on the anchor and a second portion on the hole cutter.

The conversion means may comprise a thread. More preferably, the conversion means comprises a first thread on the anchor, configured to engage a second thread on the hole cutter. Advantageously the conversion means comprising a first and a second thread allows for the properties of the threads to be selected in dependence on the material to be cut. By reducing a thread pitch (i.e. a distance between adjacent threads), the force required to rotate the hole cutter to cut the material may be reduced. By increasing a thread pitch, the force required per rotation of the hole cutter may be increased, but the number of rotations of the hole cutter required to perforate the material may be reduced.

This is particularly advantageous for perforators for drilling bone, as the thread pitch may be chosen to allow very fine control of the depth of the hole cutter as it moves through the bone.

The threads may be configured so that rotation of the hole cutter in a clockwise direction around the anchor drives the hole cutter towards the material to be cut. An alternative embodiment would also be possible in which anti-clockwise rotation of the hole cutter drives the hole cutter towards the material to be cut.

Alternatively or additionally, the conversion means may comprise a spring or an inclined surface.

A thread pitch may be selected in dependence on the diameter of the hole to be cut, and or the diameter of the threads.

Yet more preferably, the threads may have a thread pitch of between about 0.3 mm and about 2.0 mm. Advantageously, such a thread pitch ensures that the thread pitch is large enough for engagement of the threads to be stable, but that the pitch is not too large for smooth engagement and cutting.

Preferably, the threads may have a thread pitch of between about 0.3 mm and 1.0 mm, more preferably between about 0.4 mm and about 0.6 mm, or yet more preferably about 0.5 mm. Thread pitches in this range are particularly suitable for use in a perforator where fine control of the cutting is required.

The term "about" refers herein to an approximate value, the approximate value being within about 10% of the stated value, or within about 5% of the stated value, or within about 2% of the stated value.

Preferably, the anchor, at a distal end, comprises a screw tip for securing to the material to be cut. More preferably, the screw tip may be self-drilling. Advantageously, the anchor may be easily and safely secured to the material to be cut. The length of the screw tip, and the pitch of the screw tip, may be adjusted according to the material to be cut. The length of the screw tip is preferably less than the thickness of the material to be cut.

In particular, if a hole is to be drilled in a skull, the length of the screw tip may be selected so as to ensure that the anchor is safely secured to the skull so as to provide sufficient resistance to a traction force acting on the anchor as the cutting head is rotated to cut the material. However, the screw tip must not be so long as to completely penetrate the skull.

The term "distal" refers herein to portions of the apparatus, and portions of individual components of the apparatus, positioned towards the material to be cut when the apparatus is in use, while the term "proximal" refers to portions of the perforator that are further from the material to be cut and closer to, for example, the hand of a user, when the apparatus is in use.

The thread pitch and thread shape of the screw tip may be selected such that the anchor may resist a traction force. Thus when the hole cutter is rotated around the anchor and begins to cut the material, the traction force transmitted back to the anchor does not cause the anchor to unscrew from its position in the material to be cut.

Preferably, the length of the screw tip may be between about 2 mm and about 5 mm. More preferably, the length of the screw tip may be between about 2.5 mm and about 4 mm. Yet more preferably, the length of the screw tip may be about 3 mm.

Preferably, the anchor comprises an abutment surface adjacent a proximal end of the screw tip. The abutment surface has a larger diameter than the screw tip, and is configured to abut the material to be cut once the screw tip has been screwed into the material to the intended depth. The abutment surface may advantageously limit how far the anchor can be screwed into the material to be cut, and allow the anchor to be safely secured to the material to be cut. In particular, a large abutment surface area between the material to be cut and the abutment surface of the anchor may prevent tilting of the anchor.

Preferably, the anchor is a self-drilling screw comprising the self-drilling screw tip at a distal end, and a shank extending from the screw tip to a proximal end. At a distal end, the shank terminates in the abutment surface. More preferably, the shank comprises the first portion of the conversion means, which may be the first thread.

Preferably, the hole cutter may comprise a distal cutting head portion and a proximal shaft portion. The cutting head portion may be removable from the shaft portion. Advantageously, the cutting head portion may be replaceable, i.e. cutting head portions of differing diameter may be attached to the same shaft portion, so that the same shaft portion may be used for cutting a hole of differing diameter.

More preferably, the cutting head portion may comprise a first attachment. The first attachment may be an injection-moulded part. Advantageously, the hole cutter may be suitable for single use only, which may help to ensure that the apparatus is sterile when used.

Yet more preferably, the first attachment may be configured to engage a second attachment of the shaft portion. The shaft portion may comprise the second portion of the conversion means, which may be the second thread.

The cutting head portion may be conical. Preferably, an outside diameter of the cutting head portion is conical and an inside diameter of the cutting head is conical. More preferably, the angle of the conical portion is less than 5 degrees, preferably less than 3 degrees. The cutting head being conical allows a piece of material to be more easily removed from the hole cut in the material. This may be particularly advantageous when the material to be cut is living tissue, and the piece of material is e.g. a bone flap.

Preferably, the hole cutter comprises a locking arrangement configured to permit rotational motion of the hole cutter around the anchor only when a user does not apply a force in a direction towards the material to be cut. More preferably, the locking arrangement is configured to permit rotational motion of the hole cutter around the anchor only when a user applies a force in a direction away from the material to be cut. This may advantageously act as a safety feature to prevent a user from inadvertently applying forward pressure during cutting.

Preferably, the hole cutter comprises a cutter drive portion. The cutter drive portion may form part of the locking arrangement. The cutter drive portion may be provided on an outer surface of the hole cutter. More preferably, the cutter drive portion comprises at least one notch. Alternatively or additionally, the cutter drive portion may comprise at least one projection, or the cutter drive portion may have an angular profile like a nut, but the function of the cutter drive portion will be described below by reference to a notch.

The at least one notch may be an axial notch. Preferably, the at least one notch is located towards a proximal end of the hole cutter. Preferably, the at least one notch is a plurality of notches. More preferably, the plurality of notches is arranged around a circumference of the hole cutter. Yet more preferably, the plurality of notches is arranged evenly around the circumference of the hole cutter.

The term "axial" refers herein to a direction parallel to the longitudinal axis of the anchor, hole cutter, or apparatus, i.e. movement in "a direction towards the material" is a movement in an axial direction.

Preferably, the anchor comprises an anchor drive surface. More preferably, the anchor drive surface is at a proximal end of the anchor.

Preferably, the apparatus comprises a drive tool, more preferably a multifunctional drive tool. The drive tool is configured to engage at least one of the hole cutter and the anchor. Engagement of the drive tool with the hole cutter and/or the anchor may be reversible.

More preferably, the drive tool comprises a first tool drive portion configured to engage the cutter drive portion, and/or a second tool drive portion configured to engage the anchor drive surface.

Alternatively, the apparatus may comprise separate drive tools for engaging the hole cutter and the anchor. Nevertheless, a single drive tool configured to separately engage both the anchor and the hole cutter is preferable. In particular, a single drive tool which can engage both the anchor and the hole cutter, but is configured to engage only one of the anchor and the hole cutter at a time, may ensure that the anchor and the hole cutter are not driven at the same time.

Advantageously, the drive tool may facilitate securing the anchor to the material to be cut. By engaging the anchor drive surface, rotational motion of the drive tool may be transmitted to the anchor so that the anchor can be screwed into the material to be cut. As such, the user does not have to apply rotational motion to the narrow anchor directly, but may do so via the more easily accessible and convenient drive tool.

Additionally or alternatively, the drive tool may facilitate imparting rotational motion on the hole cutter. In particular, it may be difficult to provide sufficient force to the hole cutter to overcome the resistance of the material to be cut. As such, by allowing the drive tool to engage the at least one notch of the hole cutter, the user does not have to apply rotational motion to the hole cutter directly, but may do so via the more easily accessible drive tool.

Preferably, the drive tool is elongate so as to provide a lever and/or a handle for facilitating rotation of the hole cutter and/or anchor.

The drive tool may alternatively be an integral part of the anchor and/or the cutting head. The drive tool may comprise two portions, an anchor drive tool portion which is an integral part of the anchor and a cutting head drive tool portion which is an integral part of the cutting head. Alternatively, if the drive tool is an integral part of the anchor and cutting head, the drive tool may preferably be configured so that rotational motion of the drive tool is selectively transmitted to the anchor or the cutting head.

The drive tool preferably comprises a cavity for receiving a proximal portion of the anchor. The proximal portion of the anchor comprises the anchor drive surface. Preferably, the drive tool, within the cavity, comprises a corresponding first tool drive surface, configured to engage the anchor drive surface. Advantageously, the cavity of the drive tool allows quick and reversible engagement of the drive tool with the anchor. Preferably, the drive tool further comprises clamping means within the cavity. The clamping means is configured to engage the anchor to reversibly secure the drive tool to the anchor. The clamping means may be at least one spring clip.

In an alternative embodiment, the arrangement may be reversed, and the proximal portion of the anchor may comprise a cavity for receiving a distal portion of the tool, comprising the anchor drive surface. In this alternative embodiment, the anchor may comprise clamping means within the cavity, and the drive tool comprises a protruding first tool drive portion configured to engage the anchor drive surface.

In a further alternative embodiment, a proximal portion of the anchor may comprise an anchor drive surface. The proximal portion of the anchor may comprise a slot. The slot may be configured to receive a projection extending from the drive tool. The slot may comprise clamping means, such as a spring clip. Alternatively, the projection may comprise a clamping means.

The drive tool preferably comprises a shaped opening. The shaped opening may be a spanner or a socket or nut driver. The shaped opening is configured to engage the hole cutter. Particularly preferably the spanner, socket or nut driver is configured to engage the cutter drive portion.

In a preferred embodiment, the opening is sized to fit around the circumference of the hole cutter. The inside of the spanner may comprise at least one projection configured to engage one of the at least one notch (or the at least one projection or drive surface, depending on the design of the cutter drive portion). The inside of the spanner may further comprise a second clamping means. The second clamping means may be at least one spring clip to engage the hole cutter.

The at least one axial notch of the cutter drive portion may have an open distal end. As such, the clamping of the drive tool to the hole cutter may be sufficient for rotational motion of the drive tool to be transmitted to the hole cutter, but if an axial force towards the material is exerted on the drive tool during cutting, the drive tool will disengage from the axial notch by sliding out of the open distal end of the notch, so as to prevent further rotational motion of the hole cutter.

Alternatively or additionally, the drive tool may cooperate with a cutter drive portion and/or locking arrangement of the apparatus similar to a reverse child-resistant packaging, i.e. an axial force in a direction away from the material may be required for the at least one projection of the spanner to remain engaged with the at least one groove, and engagement of the groove and the projection is required to allow the cutting head to rotate.

Preferably, the drive tool may comprise a grip opening that extends through the drive tool. Advantageously, the grip opening may allow for a user to hold onto the drive tool by gripping through the grip opening.

Any component of the apparatus, such as the anchor, the hole cutter, and the drive tool, may be reusable, or may be for single use only.

Preferably, a hardness of the screw tip, and a hardness of the cutting edge, are each greater than a hardness of the material to be cut.

In preferred embodiments, the apparatus is a perforator, such as a cranial perforator, for cutting a hole in bone tissue, particularly a skull. Alternatively, the apparatus may be a drill or a "hole cutter drill", for cutting a hole in at least one of wood, glass, metal, plasterboard or the like.

In a preferred embodiment, the invention provides a perforator for cutting a hole in bone tissue. The perforator comprises an anchor configured to be secured to bone tissue to be cut, and a hole cutter configured to rotate around the anchor and cut the bone tissue. The hole cutter is configured to engage the anchor via conversion means for converting rotational motion of the hole cutter around the anchor into linear motion of the hole cutter towards the bone tissue.

The features described above and below are applicable to the perforator, where the material to be cut is bone tissue, particularly bone tissue of a skull.

Although the apparatus for cutting a hole may be configured to be used manually, i.e. without the need for an electric drill, the apparatus may alternatively or additionally be configured for use with an electric drill. For the apparatus to be configured to be used with an electric drill, the proximal ends of the anchor and/or the cutting head, and/or the drive portions of the anchor and the cutting head may be configured so as to be engageable by an electric drill.

In a second aspect, the present invention provides a kit of parts for cutting a hole, the kit of parts comprising: an anchor configured to be secured to a material to be cut; and a hole cutter configured to engage the anchor via a conversion means and cut the material. The conversion means is configured to convert rotational motion of the hole cutter around the anchor into linear motion of the hole cutter towards the material.

Preferably, the anchor is a self-drilling screw comprising a self-drilling screw tip at a distal end, and a shank extending from the drill tip to a proximal end. At a distal end, the shank may terminate in the abutment surface. More preferably, the shank comprises a or the first thread.

More preferably, the hole cutter comprises at least one cutting edge at a distal end and, on an inner surface of the hole cutter, a second thread corresponding to the first thread.

Preferably, the kit of parts comprises a drive tool, more preferably a multifunctional drive tool. The drive tool is configured to engage at least one of the hole cutter and the anchor. Engagement of the drive tool with the hole cutter and/or the anchor may be reversible.

More preferably, the drive tool comprises a first tool drive portion configured to engage the anchor drive surface; and/or a second tool drive portion configured to engage the cutter drive portion.

The features described above in relation to the first aspect of the invention are equally applicable to the separate elements of the kit of parts. In particular, any features described in relation to the anchor, the conversion means, the hole cutter, or the drive tool, may be applied to those elements of the kit of parts.

In a third aspect, the present invention comprises a method for cutting a hole, the method comprising the steps of: securing an anchor to a material to be cut; engaging a hole cutter with the anchor via a conversion means for converting rotational motion of the hole cutter around the anchor into linear motion of the hole cutter towards the material; and rotating the hole cutter around the anchor, so that the conversion means converts the rotational motion of the hole cutter into linear motion that urges the hole cutter into the material.

Preferably, the method further comprises at least one of: engaging the anchor with a drive tool to secure the anchor to the material to be cut; engaging the hole cutter with a drive tool before rotating the hole cutter around the anchor, to facilitate rotating the hole cutter around the anchor.

The step of securing the anchor to the material to be cut preferably comprises the step of screwing a screw tip of the anchor into the material to be cut.

The conversion means preferably comprises a first thread on the anchor which is engaged with a second thread on the hole cutter, so that rotating the hole cutter around the anchor causes the second thread to move down the first thread in the direction of the material to be cut.

Any feature in one aspect of the invention may be applied to other aspects of the invention, in any appropriate combination. Furthermore, any, some and/or all features in one aspect may be applied to any, some and/or all features in any other aspect, in any appropriate combination. In particular, any product features provided in relation to the first aspect may be applied to any of the other aspects.

It should also be appreciated that particular combinations of the various features described and defined in any aspects of the invention may be implemented and/or supplied and/or used independently.

BRIEF DESCRIPTION OF THE DRAWINGS

Specific embodiments of the invention will now be described with reference to the figures, in which.

DETAILED DESCRIPTION OF THE INVENTION

Figure 1:
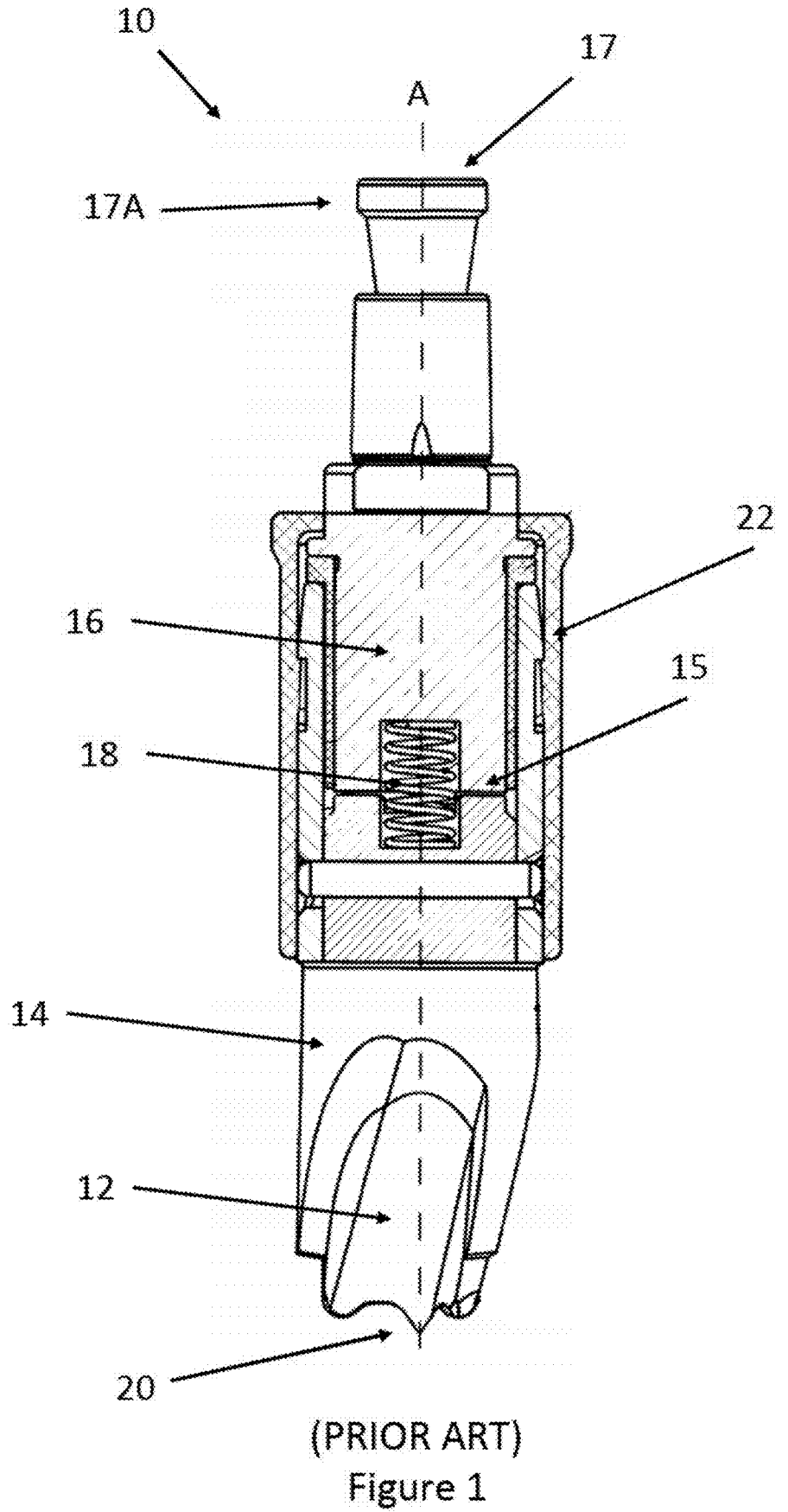
FIG. 1 is a partially cut-away side view of a perforator according to the prior art.

FIG. 1 illustrates the parts of a prior art perforator design similar to the perforator disclosed in WO 2015/150844.

In FIG. 1, the perforator 10 comprises an inner drill head 12, a hollow outer chipping head 14 arranged coaxially around the inner drill head 12, and a drive shaft 16, all rotatable about the same axis of rotation A. The drive shaft has a distal end 15 and a proximal end 17, the proximal end 17 being connectable, for example, to a hand-held drill housing a motor. In particular, the proximal end 17 is a standardised connector 17A, such as a Hudson connector.

In use, the perforator 10 must be connected to a manual or, more commonly, an electric drill. The perforator 10 is not a standalone apparatus for cutting a hole. The distal end of the perforator 10 terminates in the distal tip 20 of the inner drill head 12, which contacts bone in use, and is shown at the bottom of FIG. 1. The proximal end of the perforator 10 terminates in the standardised connector 17A of the drive shaft 16, which is shown at the top in FIG. 1.

The inner drill head 12 is movable along the rotational axis A between two positions: a distal position, in which the inner drill head 12 is not connected to the drive shaft 16, and a proximal cutting position, in which the inner drill head 12 is connected to the drive shaft 16. The inner drill head is biased away from the drive shaft 16 and into the distal position by a spring 18, so that the inner drill head only moves into the proximal cutting position when the distal tip 20 of the inner drill head 12 is pressed against a surface, such as a bone. The force with which the distal tip 20 has to be pressed against the surface to overcome the biasing force of the spring 18 is determined by the spring constant of the spring 18 and the axial separation between the distal position and the proximal cutting position.

When no pressure is applied to the distal tip 20 of the inner drill head 12, the inner drill head 12 and the drive shaft 16 are disconnected, and neither of the inner drill head 12 and the outer chipping head 14 rotates even when the drive shaft 16 is rotating. As such, the user must exert a force in a direction towards the surface of the material to be cut so that the inner drill head 12 is pressed against the surface with sufficient force to overcome the biasing force of the spring. A cylindrical housing 22 is arranged coaxially around the outer chipping head 14.

As soon as the distal tip 20 of the inner drill head 12 perforates the bone (for example the inner surface of the cranium), the force applied to the tip of the inner drill head 12 by the bone is greatly reduced, so that it is exceeded by the force exerted by the biasing spring 18 on the inner drill head 12, so that the biasing spring 18 urges the inner drill head 12 forward. As the biasing spring 18 urges the inner drill head 12 into its distal position, both the inner and outer cutting heads should cease to rotate immediately to prevent damage to the dura mater.

The present inventors have found, however, that in the prior art designs it cannot be guaranteed that the inner cutting head does not damage the dura mater. This is in part because the clutch may not disengage in time, in part because the inner drill head 12 comprises sharp projections, which are urged forward when the perforator penetrates the bone, and in part because the user must exert a force towards the material to be cut for the perforator to function. This risk is heightened because of the likelihood that the user must be pressing the perforator towards the skull at the moment that the cranium is perforated.

FIGS. 2 to 9B illustrate an apparatus 200 for cutting a hole according to a first preferred embodiment of the present invention. The illustrated apparatus 200 is a perforator for cutting a hole through bone tissue, such as through a cranium or skull.

Figure 2A:
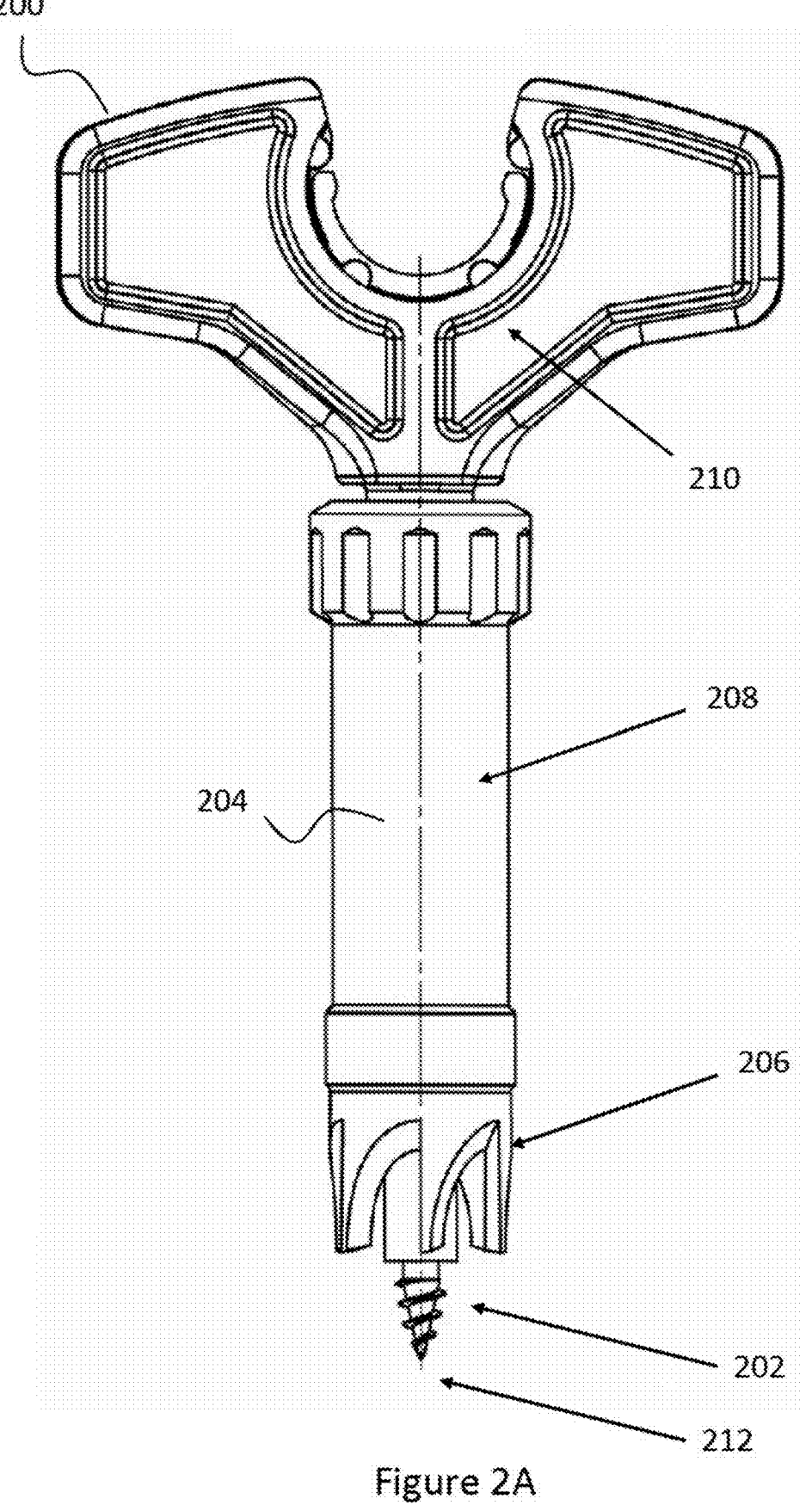
FIG. 2A is a side-on view of an example apparatus embodying the present invention.

In this preferred embodiment, as shown in FIG. 2A, the apparatus 200 comprises: an anchor 202; a hole cutter 204, which is arranged coaxially around the anchor and comprises a cutting head 206 and a shaft 208; and a drive tool 210.

Distally, the apparatus 200 terminates in a distal anchor tip 212 configured to engage the material to be cut, shown at the bottom of FIG. 2A. Proximally, the apparatus terminates in a proximal anchor end which in FIG. 2A is engaged with the drive tool 210.

The drive tool 210 is separable from the rest of the apparatus 200, but in FIG. 2A is shown engaged with the anchor 202.

Figure 8:
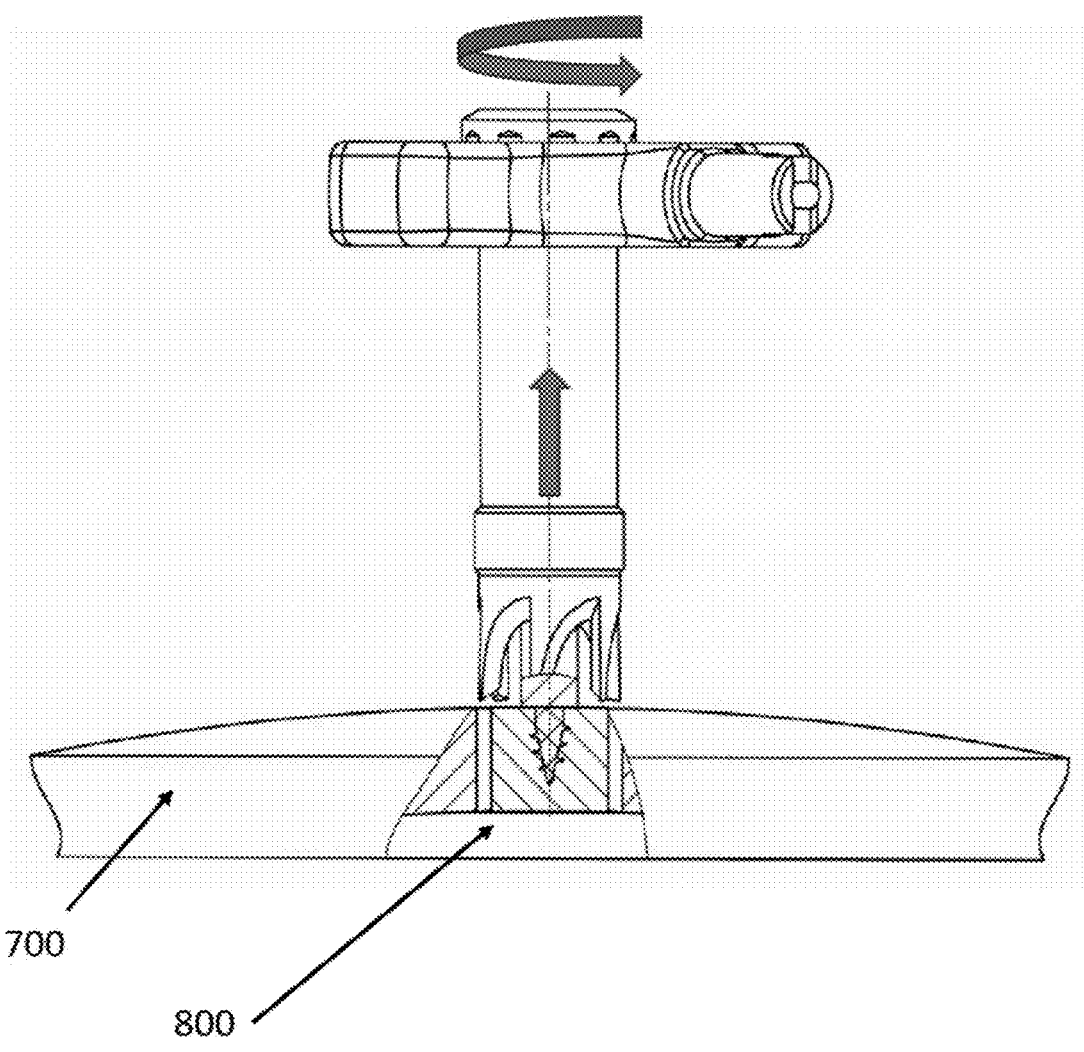
FIG. 8 is a partially cut-away side-on view of the example apparatus embodying the present invention of FIG. 7 in use, cutting a hole in the material.
Figures 9A, 9B:
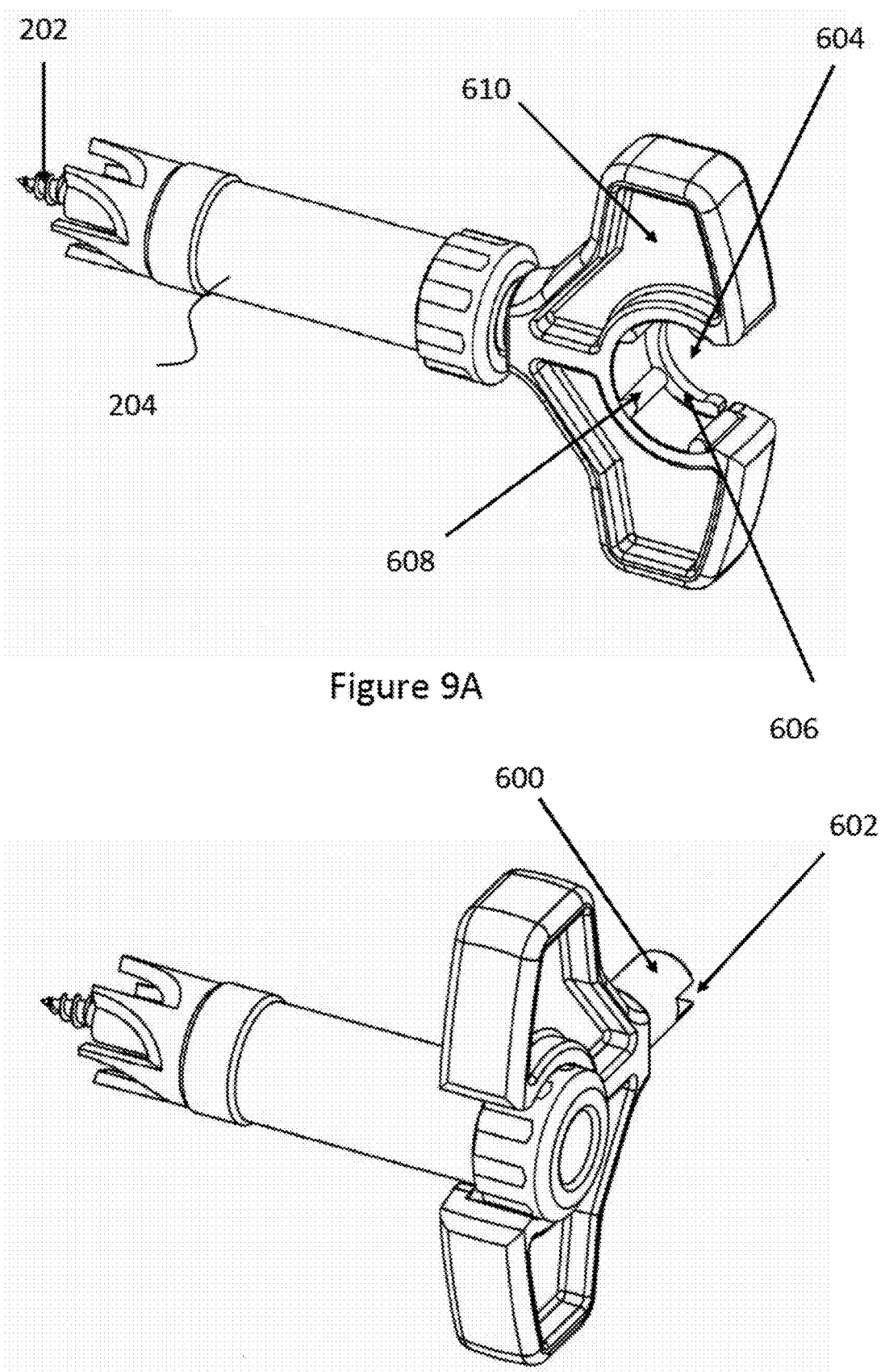
FIG. 9A is a perspective view of the example apparatus embodying the present invention of FIGS. 2 to 8.
FIG. 9B is a further perspective view of the example apparatus embodying the present invention of FIG. 9A.

In a first delivery state for securing the anchor, the drive tool 210 may be engaged with the anchor 202 as shown in FIGS. 2A and 9A. In a second delivery state for rotating the hole cutter 204, the drive tool 210 may be engaged with the hole cutter 204 as shown in FIGS. 8 and 9B.

As described below, the drive tool 210 is a multifunctional drive tool for engaging the anchor 202 as shown in FIGS. 2A and 9A to facilitate securing of the anchor 202 to the material to be cut, and for facilitating rotation of the hole cutter 204 to cut the hole in the material as shown in FIGS. 8 and 9B.

Figure 2B:
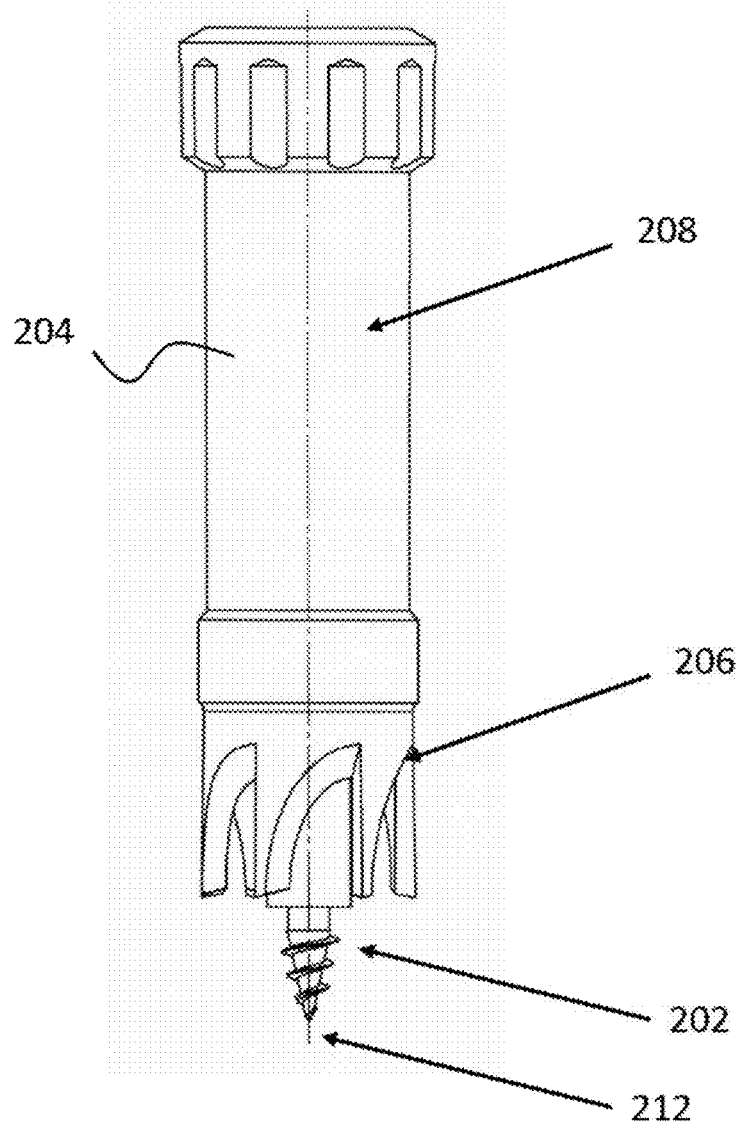
FIG. 2B is a side-on view of the example apparatus embodying the present invention of FIG. 2A with the drive tool removed.

FIG. 2B shows the anchor 202 and hole cutter 204 without the drive tool 210 attached.

Figure 3:
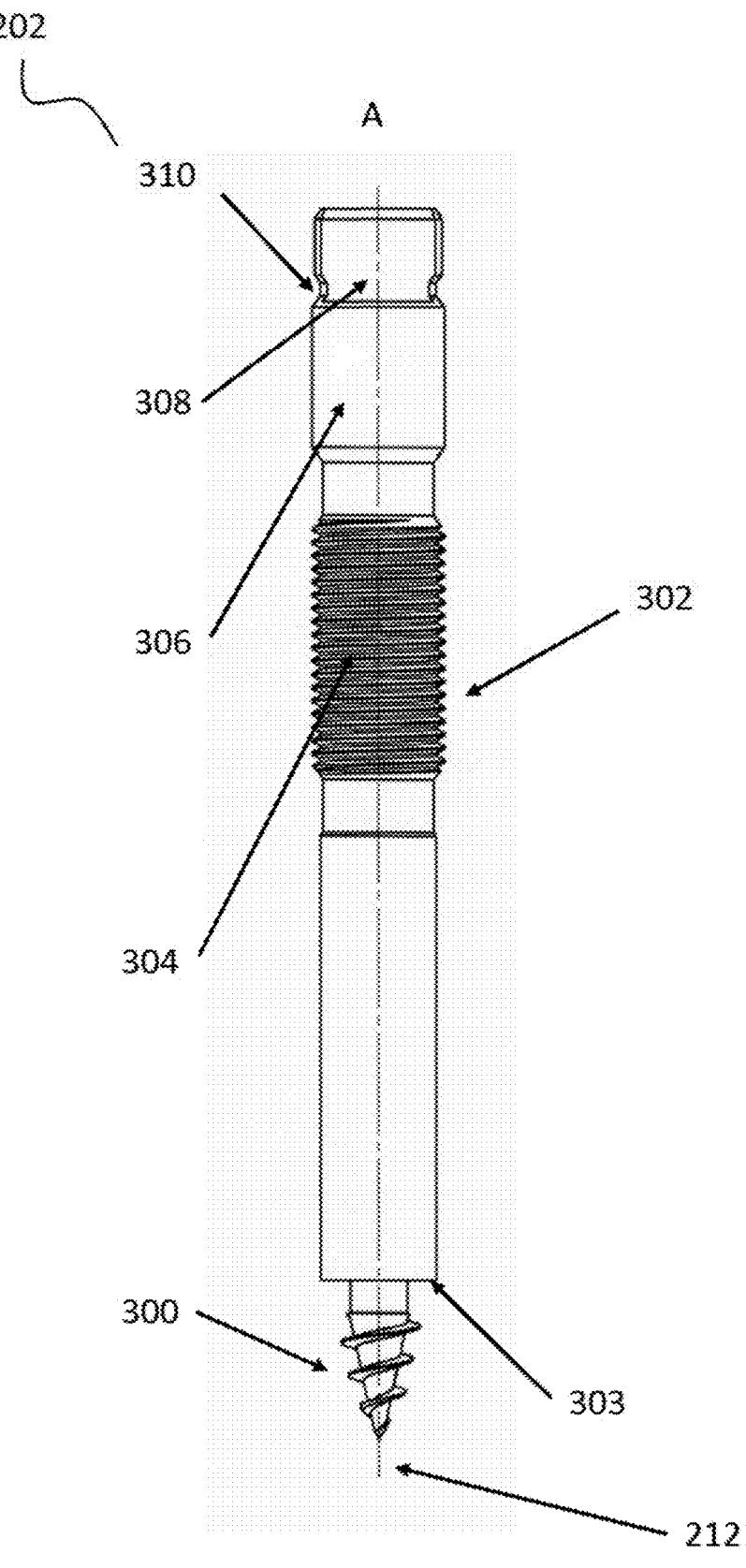
FIG. 3 is a side-on view of an example anchor of the example apparatus embodying the present invention of FIG. 2A.

As shown in FIGS. 2A, 2B and 3, the anchor 202 is a self-drilling screw extending along a longitudinal axis A. At a distal end, the anchor comprises a screw tip 300, which is self-drilling. The screw tip terminates distally in the distal tip 212.

The length of the screw tip 300 and the pitch of the thread of the screw tip 300 are selected according to the thickness and hardness of the material to be cut. If the apparatus 200 is a perforator for cutting a hole in a skull, the screw tip may be between 3 mm and 6 mm long. The pitch of the thread of the screw tip 300 determines the linear movement along longitudinal axis A, towards a material, per rotation of the anchor 202. The thread of the screw tip 300 is designed such that it can resist a traction force acting on the anchor 202.

Proximally, the screw tip 300 is connected to a shank 302, the shank 302 having at a distal end an abutment surface 303. The abutment surface 303 has a larger diameter than the screw tip 300, so that when the screw tip is fully screwed into a material to be cut, the abutment surface abuts the material to prevent further travel and indicate that the anchor is secured. The screw tip 300 is connected to the shank 302 via the abutment surface 303.

The shank 302 comprises a first thread 304, which is a male thread. The first thread 304 is part of a conversion means for engaging the anchor 202 with the hole cutter 204. The thread pitch of the threads in the conversion means determines the distance of a linear movement of the hole cutter 204 along longitudinal axis A, towards a material, per rotation of the hole cutter 204 around the anchor 202.

Proximally, the anchor 202 has an elongated pilot pin 306. At the proximal end of the pilot pin 306, the anchor 202 comprises an anchor drive surface configured to be engaged by the drive tool 210, and an indentation 310. The anchor drive surface is provided on a flat projection 308 extending from the proximal end of the anchor 202, so that a corresponding anchor drive surface on the drive tool 210 can abut the anchor drive surface and drive rotation of the anchor 202. In order to engage the flat projection 308, the anchor drive surface on the drive tool 210 may be two walls defining a slot sized to receive the projection 308.

When the projection 308 providing the anchor drive surface is engaged by the drive tool 210, rotational motion of the drive tool 210 is transmitted to the anchor 202 so that the screw tip 300 can be screwed into the material to be cut. The elongation of the pilot pin 306 allows for secure positioning and screwing in of the anchor 202 on uneven or slanted surfaces. When the screw tip 300 is fully screwed into the material to be cut, the abutment surface 303 abuts the material to be cut, and the anchor 202 is securely attached to the material.

The indentation 310 in the proximal end of the pilot pin 306 is configured to be engaged by a clamping means of the drive tool 210, so as to secure the drive tool 210 safely to the anchor 202. This also allows for easy removal of the drive tool 210 from the anchor 202 once the anchor 202 is secured to the material to be cut.

Figure 4:
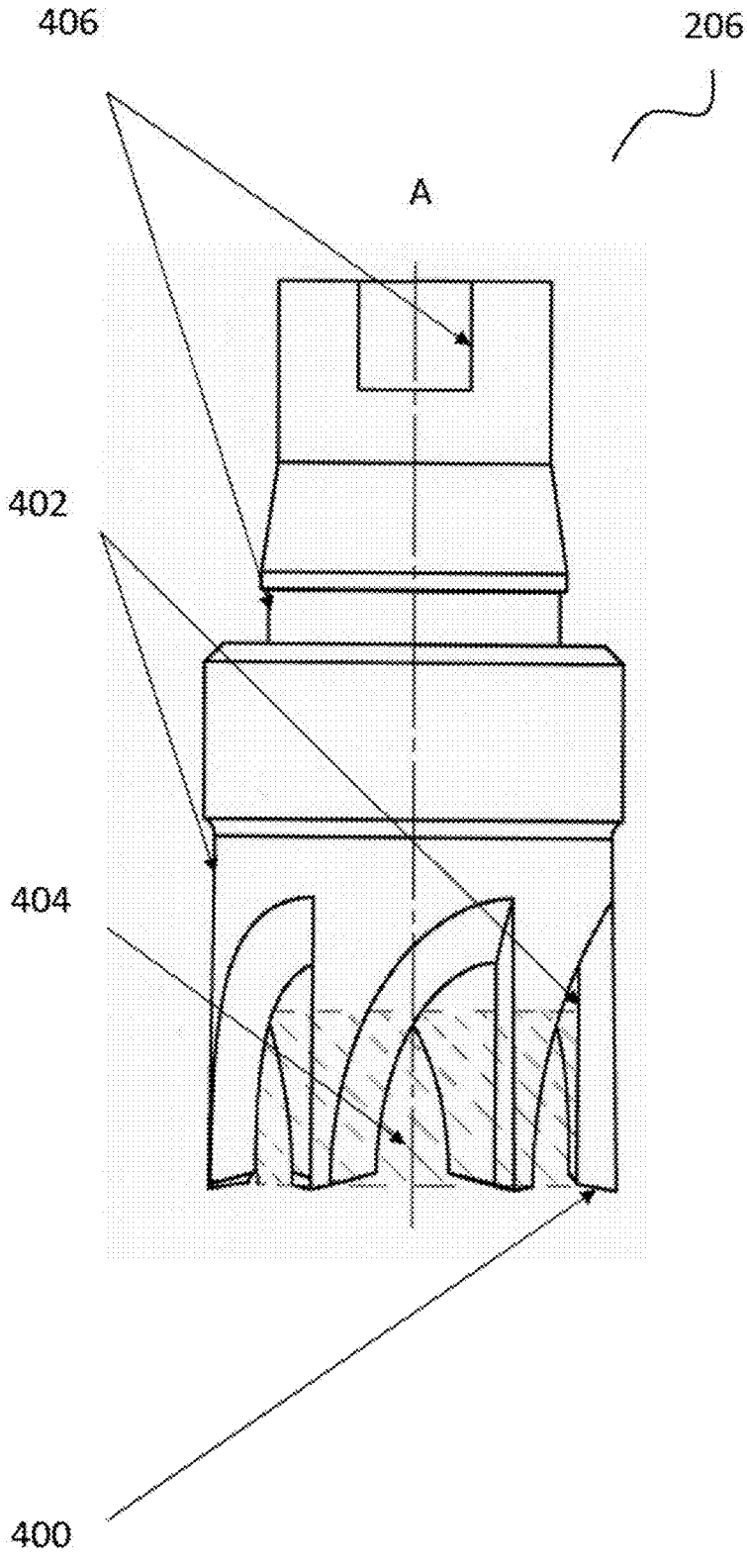
FIG. 4 is an enlarged side-on view of an example cutting head of a hole cutter of the example apparatus embodying the present invention of FIG. 2A.

FIG. 4 shows an enlarged side-on view of the cutting head 206 of the hole cutter 204. The cutting head 206 terminates distally in a plurality of cutting edges 400 or projections. The cutting edges 400 are off-set internally so as to allow the full skull to be penetrated in the full diameter of the cutting head 206. The cutting edges 400 being off-set also allows for bone chippings to be carried away from the cutting edges 400.

The outer diameter of the cutting head 206 is varied so that the cutting head has a conical profile 402 both internally and externally, so as to allow the hole cutter 204 to be easily withdrawn from the skull once a bone flap 404 has been separated from the rest of the skull. The conical profile 402 also allows for the bone flap 404 to be more easily reinserted into the hole cut in a skull.

A typical skull may have a thickness of up to 10 mm, and the cutting head 206 is designed so as to allow a hole to be cut into a skull of up to 10 mm thickness. The diameter of the hole that will be cut by the apparatus is determined by the outer diameter of the cutting head 206 at the cutting edges 400. For use as a perforator, the diameter may be around 6 mm, 8 mm, or 11 mm, or any other suitable diameter. The suitable diameter may depend on the type of neural surgery required.

Due to the properties of the cutting edges 400 and the cone-shaped outer profile of the cutting head 206, the cutting edges 400 cut around the perimeter of a bone flap 404 or bone disc. As the bone flap 404 is secured to the anchor 202 by the screw tip 300, the bone flap 404 is maintained within the cutting head 206 both during and after cutting. The diameter of the cutting edges 400 is substantially equivalent to the diameter of the bone flap 404 or bone disc being cut.

Such a bone flap 404 or bone disc may be reattached to the skull so as to close the hole cut by the apparatus 200. Reattaching the bone flap 404 or bone disc to the skull may allow for improved healing, or a reduced risk of infection, in particular when compared with to commonly used artificial calcium phosphate plugs.

Although a specific embodiment of a cutting head 206 has been described, many other embodiments could achieve the required function of cutting a material to be cut, and cutting heads for use in the present invention are not limited to the depicted embodiment.

In the preferred embodiment shown, the cutting head 206 is separable from the shaft 208 of the hole cutter 204, but these components may optionally be formed as one unit.

At a proximal end, the cutting head 206 comprises a first attachment 406 configured to engage the shaft 208 so as to attach the cutting head 206 to the shaft 208 to form the hole cutter 204.

Figure 5A:
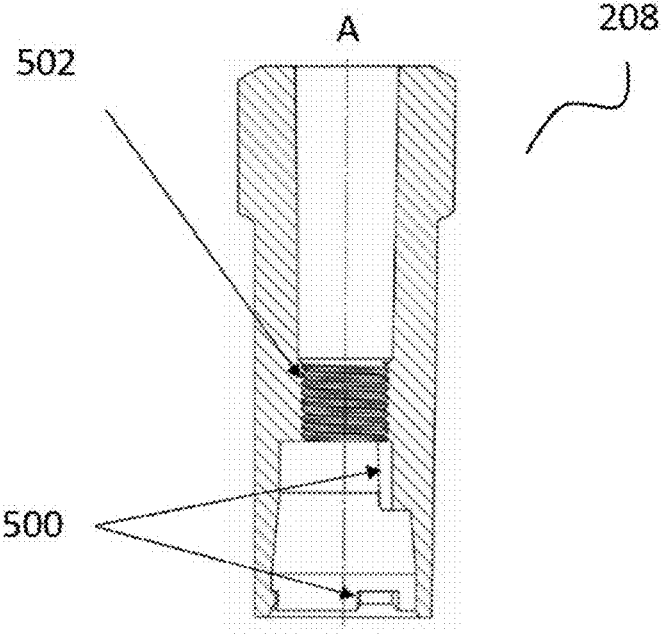
FIG. 5A is an enlarged cross-section of an example sleeve of the hole cutter of the example apparatus embodying the present invention of FIG. 2A.

As shown in the cross-section in FIG. 5A, shaft 208 internally comprises a second attachment 500, configured to cooperate with the first attachment 406, so as to allow the cutting head 206 to be securely fixed to the shaft 208. The shaft 208 further comprises a second thread 502, corresponding to the first thread 304 of the anchor 202. The second thread 502 is a female thread.

The first thread 304 and the second thread 502 are cooperating parts of a conversion means. When the apparatus is assembled, the first thread 304 engages the second thread 502, so that rotational motion of the hole cutter 204 around the anchor 202 causes the second thread to move down the first thread, so that the cutting head 206 moves in a distal direction relative to the anchor 202.

When the anchor 202 is secured to the material to be cut (bone tissue, typically forming part of a skull), the cooperation of the first thread 304 and the second thread 502 means that rotational motion of the hole cutter 204 around the anchor 202 results in a traction force on the anchor 202 and linear motion of the hole cutter 204 along the longitudinal axis A towards the material. In other words, the two engaged threads 304, 502 act as a conversion means that converts rotational motion of the hole cutter around the anchor into linear motion that urges the rotating hole cutter 204 toward and into the material to be cut.

The first attachment 406 may be an injection-moulded part, which allows for it to be produced cost-effectively. Injection-moulding of the first attachment 406 may result in the apparatus 200 being suitable for single use only, which may help to ensure that the apparatus 200 is sterile when used.

Figure 5B:
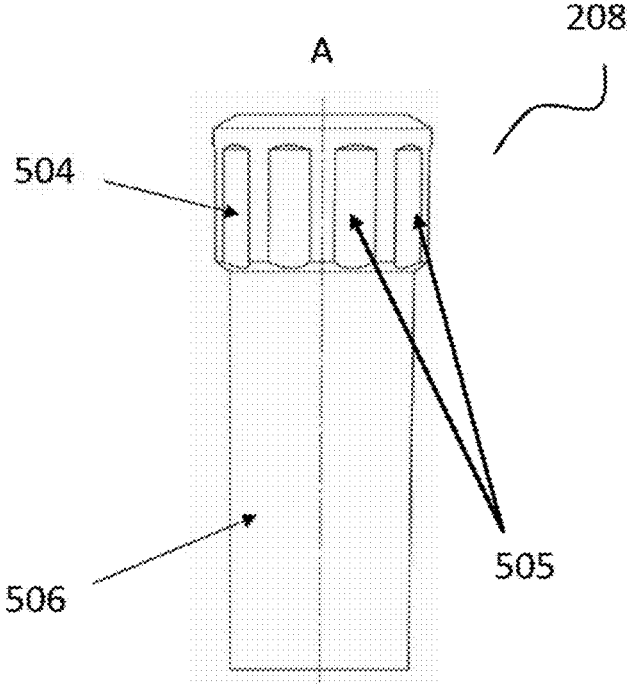
FIG. 5B is an enlarged side-on view of the example sleeve of FIG. 5A.

As shown in FIG. 5B, on the external surface of shaft 208, there is a cutter drive portion 504 at a proximal end. The cutter drive portion 504 comprises a plurality of grooves 505 or notches, which are arranged longitudinally and are open at a distal end. The grooves 505 are spaced evenly around a circumference of the shaft 208.

A clamping means of the drive tool 210 may be configured to clamp the cutter drive portion 504 and/or the grooves 505 in order to transmit rotational motion of the drive tool 210 to the hole cutter 204. In the illustrated embodiment, the outer diameter of the shaft 208 is tapered from a distal end to a proximal end. As such, the drive tool 210 can fit around the circumference of the shaft 208, and be moved in a proximal direction relative to the shaft 208, so as to engage the grooves 505 via the open distal end of the grooves 505.

Figures 6A, 6B:
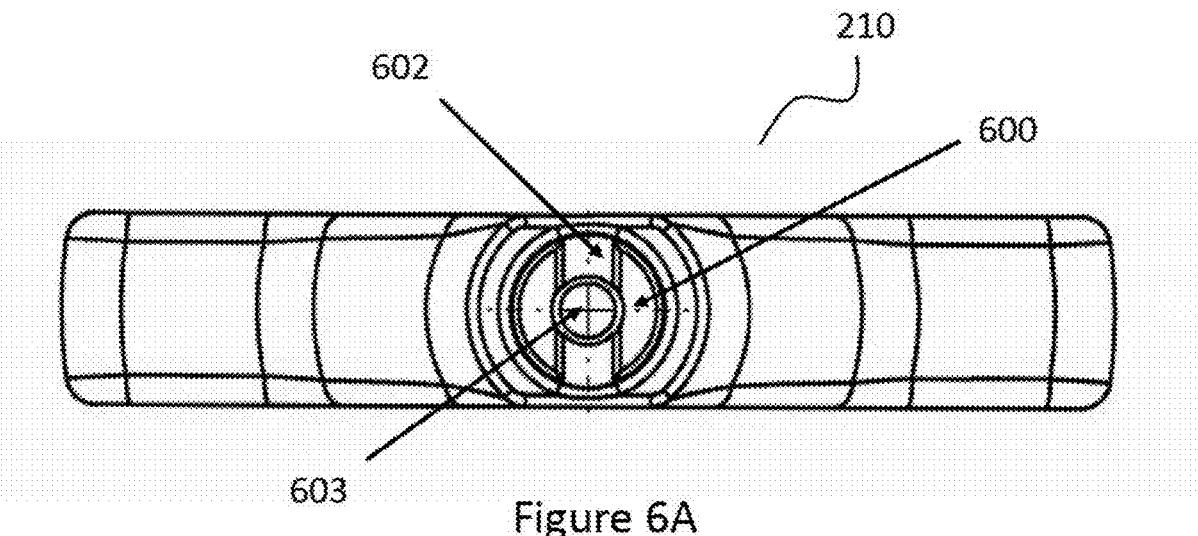
FIG. 6A is an enlarged bottom view of an example drive tool of the example apparatus embodying the present invention of FIG. 2A.
FIG. 6B is an enlarged side-on view of the example drive tool of FIG. 6A.

As shown in FIG. 6A, the drive tool 210, in a bottom view, has an elongated shape to allow the drive tool 210 to be easily gripped by hand.

As mentioned above, the drive tool 210 is separable from the apparatus 200 and is advantageously designed to engage with the anchor 202 in order to screw the anchor into the material to be cut, and also to engage with the hole cutter 204, in order to easily rotate the hole cutter 204 around the anchor. For engagement with the proximal end of the anchor 202, the drive tool 210 comprises, at a bottom surface, a projection 600 for engaging a proximal end of the anchor

202. The projection 600 comprises a central elongate slot 602 corresponding to the projection 308 carrying the anchor drive surface. The slot 602 is sized to receive the projection 308 of the anchor 202 providing the anchor drive surface so as to transmit rotational motion of the drive tool 210 to the anchor 202. This means that the anchor 202 can be secured to the material to be cut by positioning the screw tip 300 at the desired point on e.g. a skull, engaging the drive tool 210 with the proximal end of the anchor 202, and rotating the drive tool to screw the anchor 202 into the skull until the abutment surface 303 contacts the skull.

Inside the slot 602, the drive tool 210 may further comprise a clamping means (not shown) such as a spring clip, which may be configured to engage indentation 310 of the anchor 202. In this manner, the drive tool 210 may be secured to the anchor 202 so as to transmit rotational motion, but may also be easily disengaged from the anchor 202, e.g. by pulling on the drive tool 210 in a proximal direction, once the anchor 202 is secured to the material to be cut.

The slot 602 of the projection 600 may further comprise a central circular cavity 603. The slot 602 splits the distal end of the projection 600 such that it comprises two prongs 605 configured to engage either side of the projection 308 of the anchor. This can further be seen in FIGS. 8 and 9B.

As shown in FIG. 6B, on an opposite end of the drive tool 210 relative to the cavity 600, the drive tool 210 comprises a part-circular recess 604 which forms an open-ended spanner. The recess 604 is sized so as to be able to engage the shaft 208 of the hole cutter 204. Within the recess 604, the drive tool 210 comprises at least one clamping mechanism such as a spring clip 606. The drive tool 210 further comprises multiple projections 608 arranged within the recess 604.

The drive tool 210 is configured to engage the hole cutter 204 by placing the open-ended spanner around the shaft 208 so that the shaft 208 is placed within the recess 604. By moving the drive tool 210 axially, in a proximal direction, the drive tool 210 engages the grooves 505 of the cutter drive portion 504. The projections 608 on the drive tool 210 engage the grooves 505 on the anchor 202, and the spring clip 606 clamps the drive tool 210 in place on the hole cutter 204.

In this way, the drive tool 210 is secured in position relative to the hole cutter 204 so as to allow the hole cutter to be rotated around the anchor by rotating the drive tool 210. However, because the clamping force of the spring clips 606 is relatively low, the drive tool 210 disengages from the cutter drive portion 504 easily if an axial force in a direction towards the material to be cut is exerted on the drive tool 210, as the projections 608 slip out of the open distal ends of the grooves 505.

The drive tool 210 further comprises an opening 610 extending through the drive tool so as to provide a handle or grip for a user to engage, as further shown in FIG. 9A.

As such, the cutter drive portion 504 and the drive tool 210 prevent the user from exerting a force in the direction of the material to be cut at the same time as cutting the material. Therefore, any risk of damage to anything underlying the material to be cut may be avoided.

When the perforator is used to cut a hole in a skull, there may advantageously be no risk of damage to the dura mater.

In an alternative embodiment of the apparatus 200 which is instead adapted for another purpose, such as to cut a hole in plasterboard, there may be no risk of damage to an underlying electric cable or pipe.

Figure 7:
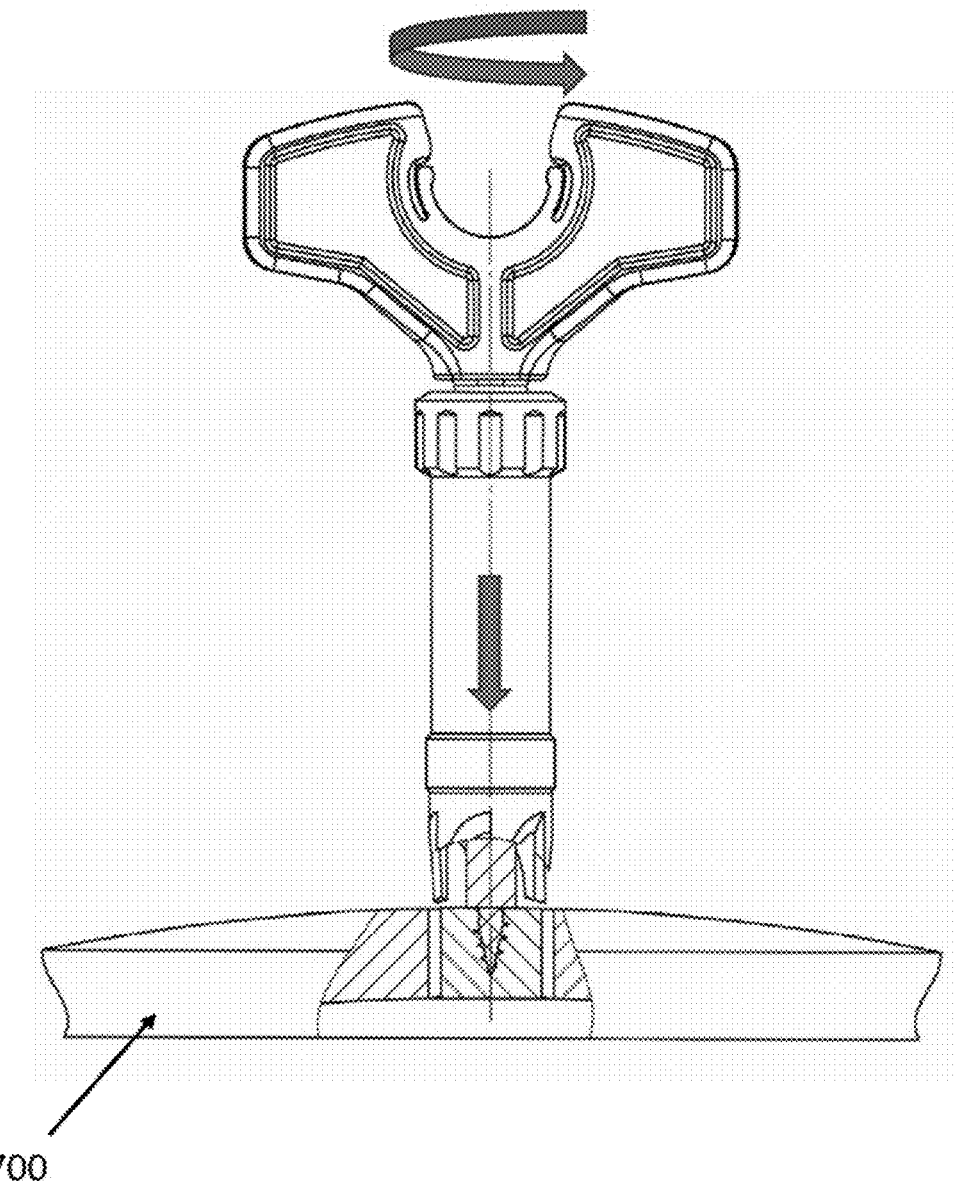
FIG. 7 is a partially cut-away side-on view of an example apparatus embodying the present invention in use, being secured to a material to be cut.

FIGS. 7 and 8 show the apparatus 200 being used to cut a hole in a skull 700, and the forces acting on the apparatus 200 in use.

To secure the apparatus 200 to the skull 700, the drive tool 210, which is shown in FIG. 7 attached to the anchor 202 at a proximal end, is rotated and an axial force in an direction towards the material to be cut must be exerted. This causes the screw tip 300 of the anchor 202 to penetrate the skull 700, until the abutment surface 303 of the shaft 302 abuts the surface of the skull 700.

The drive tool 210 is then removed from the proximal end of the anchor 202 and the recess 604 of the drive tool 210 is pushed into engagement with the cutter drive portion 504 of the shaft 208. As shown in FIG. 8, for the hole cutter 204 to cut a perforation 800 or hole into the skull 700, the drive tool 210 merely has to be rotated around the anchor 202.

As the drive tool 210 is rotated around the anchor 202 causing the hole cutter 204 to rotate along with the drive tool 210, the interaction of the first thread 304 and the second thread 502 cause the rotational motion of hole cutter 204 around the anchor 202 to be converted into a linear motion of the hole cutter 204 towards the skull 700. This causes the cutting edges 400 to be gradually pressed into the skull, and to cut the skin and bone tissue. The linear motion of the hole cutter 204 towards the skull also causes traction on the anchor 202.

As the engaged screw threads 304, 502 convert rotational motion into a force that urges the cutting head 206 through the skull 700, there is no need for the user to press the apparatus 200 into the skull 700 while cutting. In fact, any attempt to press the apparatus 200 towards the skull will cause the drive tool 210 to disengage from the cutter drive portion 504. This advantageously ensures that the skull is cut gradually and gently, with greatly reduced risk of accidental damage to the dura mater.

When the cutting head 206 finishes cutting through the skull 700, the bone flap 404 remains attached to the anchor 202, and the bone flap 404 can be easily removed to leave a circular hole. The bone flap 404 may be used to seal the hole cut into the skull 700, which may advantageously result in improved healing.

Figure 10A:
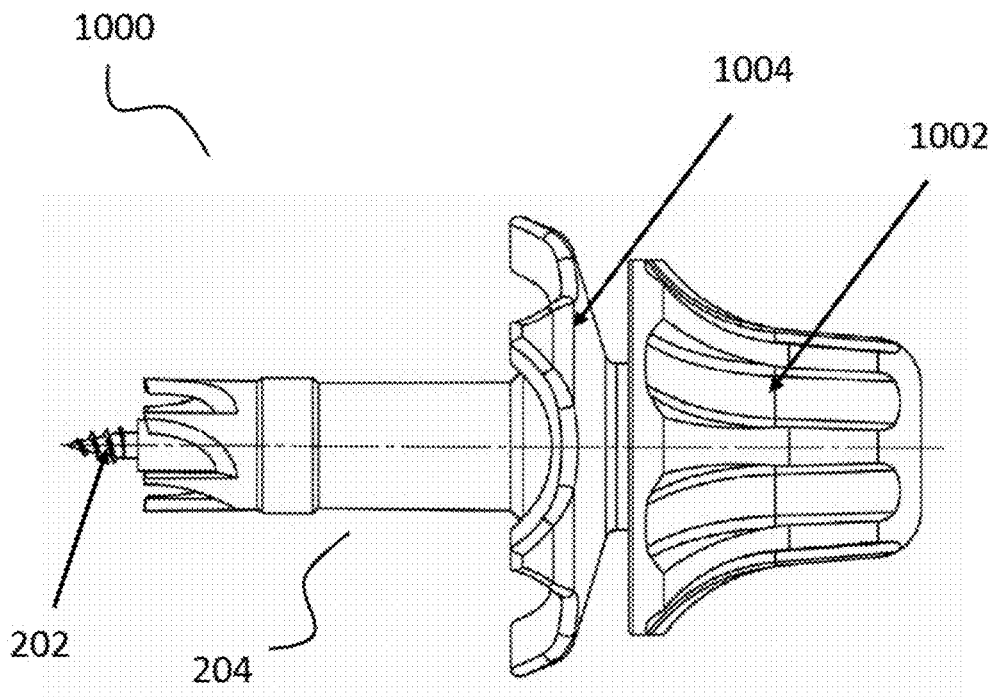
FIG. 10A is a side-on view of a second example apparatus embodying the present invention.
Figure 10B:
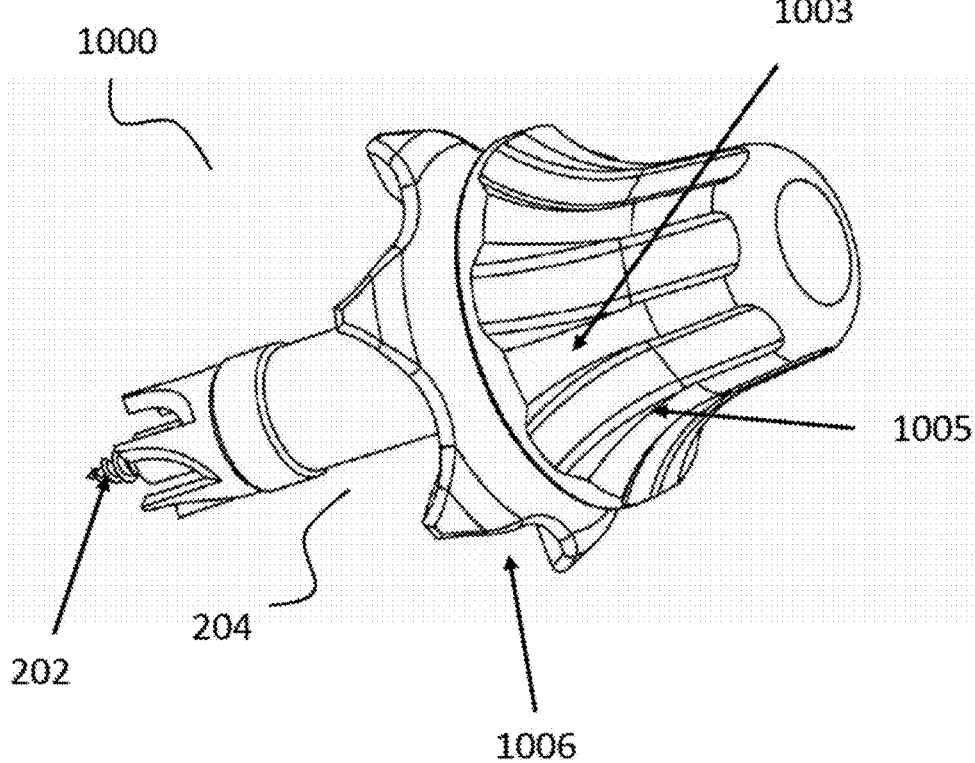
FIG. 10B is a perspective view of the second example apparatus embodying the present invention of FIG. 10A.

An alternative embodiment of the apparatus of the present invention is shown in FIGS. 10A and 10B, in which a perforator apparatus 1000 comprises an anchor 202 and a hole cutter 204 which may be identical to the anchor and hole cutter of other embodiments. However, as the apparatus 1000 shown in FIGS. 10A and 10B does not comprise a separate drive tool, but instead comprises anchor handle 1002 and cutter handle 1004.

Anchor handle 1002 is connected to anchor 202, so that rotational motion of handle 1002 is transmitted to anchor 202. This facilitates securing of the anchor 202 to a material to be cut, as the user can screw the anchor into the material to be cut by rotating the anchor handle 1002. The anchor handle 1002 comprises a plurality of grooves 1003 and ridges 1005 so that it can be securely gripped by a user, or a robotic manipulator.

Cutter handle 1004 is connected to hole cutter 204, so that rotational motion of cutter handle 1004 is transmitted to hole cutter 204. This facilitates rotating of the hole cutter 204 around the anchor 202 once the anchor 202 is secured to the material to be cut, as the user can rotate the hole cutter 204 by rotating the cutter handle 1004. The cutter handle 1004 has a larger diameter than anchor handle 1002, and a plurality of grooves 1006, so that it can be easily gripped by a user, or a robotic manipulator, even after the anchor 202 has been secured to the material to be cut.

The operation of apparatus 1000 is the same as that of apparatus 200, except that the anchor 202 and the hole cutter 204 are rotated by anchor handle 1002 and cutter handle 1004 respectively, rather than with a separate drive tool.

Figure 11A:
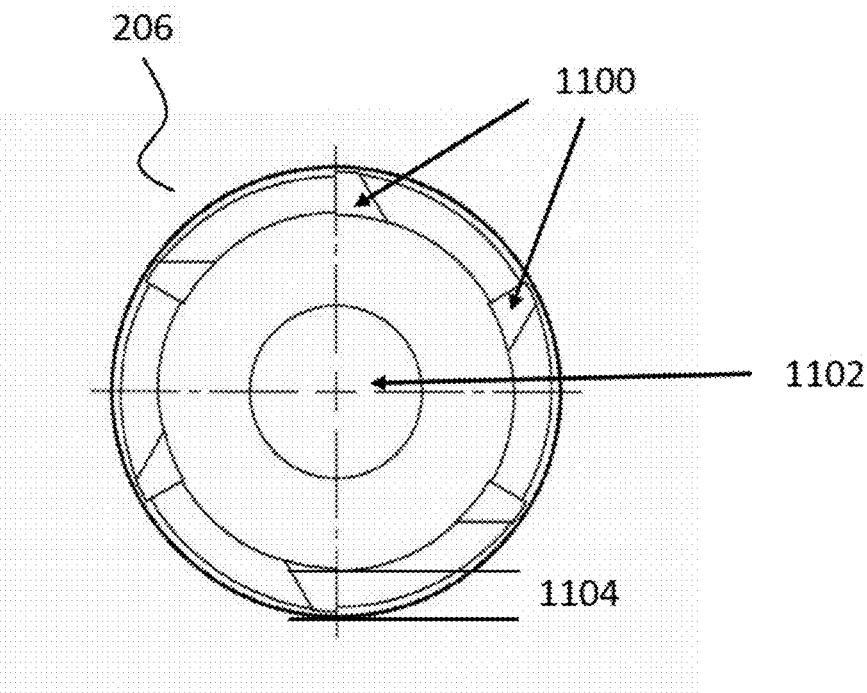
FIG. 11A is an enlarged bottom view of a cutting head of an example apparatus embodying the present invention.

FIG. 11A shows a bottom view of an example cutting head 206 having six cutting edges 1100. Centrally, the cutting head 206 comprises a cylindrical cavity 1102 through which, in use, the anchor 202 extends. The cutting edges 1100 of the cutting head 206 have a width 1104 of between about 1.0 mm and about 1.2 mm.

Figure 11B:
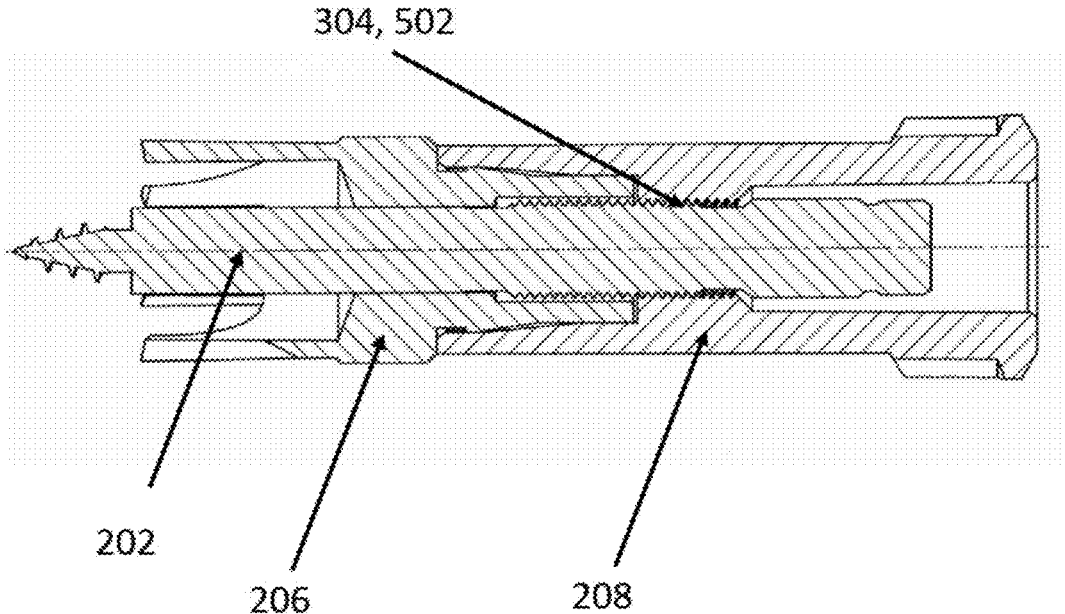
FIG. 11B is a cross-section of an anchor and a hole cutter of an example apparatus embodying the present invention.

FIG. 11B shows a cross-section of an anchor 202, engaged with shaft 208 of a hole cutter via threads 304, 502. The shaft 208 at a proximal end is attached to a cutting head 206.

As mentioned above, alternative embodiments of the apparatus 200 may be used to cut plasterboard, wood, or other materials. In such embodiments, the hole cutter may have a larger diameter, but the rest of the apparatus may be as described above, and the method of use may be identical, i.e. the anchor is fixed to the material to be cut e.g. the plasterboard, and the hole cutter is rotated around the anchor to cut the hole.

The invention claimed is:

1. A perforator for cutting a hole in bone tissue, the perforator comprising:

an anchor comprising a screw tip that comprises one or more surface features extending outwardly and engageable with bone tissue;

a hole cutter rotatably positioned around the anchor and engaged with the anchor via at least one of threads, a biasing assembly, or an inclined surface to convert rotational motion of the hole cutter around the anchor into linear motion of the hole cutter towards the bone tissue; and a drive tool configured to engage the anchor and to engage the hole cutter, the drive tool comprising:

a first tool drive portion configured to engage the anchor; and a second tool drive portion configured to engage the cutter.

2. A perforator according to claim 1, wherein the at least one of the threads, the biasing assembly, or the inclined surface converts the rotational motion of the hole cutter around the anchor into the linear motion towards the bone tissue when a counterforce, away from the bone tissue, acts on the anchor due to a disc portion of the bone material formed from the hole cutter being connected to a remaining portion of the bone material.

3. A perforator according to claim 1, wherein:

the anchor defines a central axis;

the hole cutter comprises at least one cutting edge disposed at a radius r from the central axis of the anchor; and the hole cutter is configured to form a hole in the bone material having a diameter d=2r.

4. A perforator according to claim 1, wherein the at least one of the threads, the biasing assembly, or the inclined surface comprises a first portion disposed on the anchor and a second portion disposed on the hole cutter.

5. A perforator according to claim 4, wherein the threads comprises a first thread disposed on the anchor and engageable with a second thread disposed on the hole cutter.

6. A perforator according to claim 5, wherein the threads have a thread pitch of between 0.3 mm and 2.0 mm.

7. A perforator according to claim 1, wherein the anchor comprises an abutment surface adjacent a proximal end of the screw tip.

8. A perforator according to claim 1, wherein the hole cutter comprises a cutting head and a shaft, wherein the cutting head is removable from the shaft.

9. A perforator according to claim 1, wherein the hole cutter comprises a cutter drive portion.

10. A perforator according to claim 1, wherein the anchor comprises an anchor drive surface.

11. A perforator according to claim 1, wherein:

the anchor comprises an anchor drive surface, and the first tool drive portion is configured to engage the anchor drive surface; and the hole cutter comprises a cutter drive portion, and the second tool drive portion is configured to engage the cutter drive portion.

12. A perforator according to claim 1, in which: the anchor is connected to an anchor handle, and/or the hole cutter is connected to a cutter handle.

13. A kit of parts for cutting a hole in bone tissue, the kit of parts comprising:

an anchor comprising a screw tip that comprises one or more surface features extending outwardly and engageable with bone tissue;

a hole cutter rotatably positioned around the anchor and engaged with the anchor via at least one of threads, a biasing assembly, or an inclined surface to convert rotational motion of the hole cutter around the anchor into linear motion of the hole cutter towards the bone tissue; and a drive tool configured to engage the anchor and to engage the hole cutter, the drive tool comprising:

a first tool drive portion configured to engage the anchor; and a second tool drive portion configured to engage the cutter.

14. A kit of parts according to claim 13, wherein the anchor is a self-drilling screw comprising a self-drilling screw tip at a distal end, and a shank extending from the screw tip to a proximal end, wherein a portion of the shank comprises a first thread; and wherein the hole cutter comprises at least one cutting edge at a distal end and, on an inner surface of the hole cutter, a second thread for engaging with the first thread.

15. A method of cutting a hole, the method comprising the steps of:

securing an anchor to bone tissue, the anchor comprising a screw tip wherein the screw tip comprises one or more surface features extending outwardly and engageable with the bone tissue;

engaging a hole cutter with the anchor via at least one of threads, a biasing assembly, or an inclined surface to convert rotational motion of the hole cutter around the anchor into linear motion of the hole cutter towards the bone tissue; and rotating the hole cutter around the anchor to urge the hole cutter into the bone tissue.

16. A method according to claim 15, in which the step of securing the anchor to the bone tissue comprises the step of screwing the screw tip of the anchor into the bone tissue.

\* \* \* \* \*